(12) United States Patent
Whalen, III et al.

(10) Patent No.: US 11,376,344 B2
(45) Date of Patent: *Jul. 5, 2022

(54) SYSTEM FOR SUTURELESS CLOSURE OF SCLERAL PERFORATIONS AND OTHER OCULAR TISSUE DISCONTINUITIES

(71) Applicant: UNIVERSITY OF SOUTHERN CALIFORNIA, Los Angeles, CA (US)

(72) Inventors: John J. Whalen, III, Pasadena, CA (US); Niki Bayat, Los Angeles, CA (US); Yi Zhang, Cypress, CA (US); Paulo Falabella, Newton, MA (US); Mark E. Thompson, Anaheim, CA (US); Mark S. Humayun, Glendale, CA (US)

(73) Assignee: University of Southern California, Los Angeles, CA (US)

( * ) Notice: Subject to any disclaimer, the term of this patent is extended or adjusted under 35 U.S.C. 154(b) by 44 days.

This patent is subject to a terminal disclaimer.

(21) Appl. No.: 16/693,646

(22) Filed: Nov. 25, 2019

(65) Prior Publication Data

US 2020/0085995 A1 Mar. 19, 2020

Related U.S. Application Data

(62) Division of application No. 15/013,632, filed on Feb. 2, 2016, now Pat. No. 10,512,707.

(Continued)

(51) Int. Cl.
*A61L 24/06* (2006.01)
*A61L 24/00* (2006.01)
*A61L 15/60* (2006.01)
*A61F 9/007* (2006.01)
*A61B 17/00* (2006.01)

(52) U.S. Cl.
CPC .......... *A61L 24/0031* (2013.01); *A61L 15/60* (2013.01); *A61L 24/0015* (2013.01); *A61L 24/06* (2013.01); *A61B 2017/005* (2013.01); *A61F 9/007* (2013.01); *A61L 2430/16* (2013.01)

(58) Field of Classification Search
CPC ... C08L 33/26; C08F 2220/1825; A61L 15/60
See application file for complete search history.

(56) References Cited

U.S. PATENT DOCUMENTS

2007/0224241 A1 9/2007 Stayton et al.
2012/0109035 A1 5/2012 Zhang et al.
2012/0231072 A1* 9/2012 Kang-Mieler ........... A61K 9/06
424/451

FOREIGN PATENT DOCUMENTS

WO 2009/097561 A1 8/2009
WO 2013/181713 A1 12/2013

OTHER PUBLICATIONS

Chen, G.G. et al., "Graft Copolymers that Exhibit Temperature-Induced Phase Transitions Over a Wide Range of pH," Nature, Jan. 5, 1995, v. 373, n. 6509, pp. 49-52.

(Continued)

*Primary Examiner* — Mark S Kaucher
(74) *Attorney, Agent, or Firm* — Brooks Kushman P.C.

(57) ABSTRACT

The present disclosure describes, among other things, a thereto-responsive hydrogel comprising a PNIPAM copolymer having adhesive properties that are temperature dependent, as well as a device for administering the hydrogel, and methods for making and using the foregoing.

7 Claims, 7 Drawing Sheets

Related U.S. Application Data

(60) Provisional application No. 62/110,851, filed on Feb. 2, 2015.

(56) References Cited

OTHER PUBLICATIONS

Gutowska, A. et al., "Heparin Release from Thermosensitive Polymer Coatings: In vivo Studies," J. of Biomedical Materials Research, Jul. 1995, v. 29, n. 7, pp. 811-821 (first published online Sep. 13, 2004).

Kaja, S. et al., "Evaluation of Tensile Strength of Tissue Adhesives and Sutures for Clear Corneal incisions Using Porcine and Bovine Eyes, with a Novel Standardized Testing Platfom," Clinical Opthalmology, Feb. 28, 2012, n. 6, pp. 305-309.

Lopez-Guajardo, L. et al., "Experimental Model to Evaluate Mechanical Closure Resistance of Sutureless Vitrectomy Sclerotomies Using Pig Eyes," Investigative Ophthalmology & Visual Science, v. 52, n. 7, Jun. 2011, pp. 4080-4084.

Wahjudi, P.N. et al., "Improvement of Metal and Tissue Adhesion on Surface Modified Parylene," C. Journal of Biomedical Materials Research, Part A, v. 89A, n. 1, pp. 206-214.

\* cited by examiner

SYSTEM FOR SUTURELESS CLOSURE OF SCLERAL PERFORATIONS AND OTHER OCULAR TISSUE DISCONTINUITIES

CROSS-REFERENCE TO RELATED APPLICATIONS

This application is a divisional of U.S. Ser. No. 15/013,632 filed Feb. 2, 2016, now U.S. Pat. No. 10,512,707 B2 issued Dec. 24, 2019, which claims the benefit of U.S. Provisional Patent Application No. 62/110,851, filed Feb. 2, 2015, the disclosures of which are hereby incorporated in their entirety by reference herein.

STATEMENT REGARDING FEDERALLY SPONSORED RESEARCH

This invention was made with Government support under Contract No. W81X-WH12-1-0314, awarded by the Telemedicine and Advance Technology Research Center (TATRC) of the United States Army. The Government has certain rights in the invention.

This application is also related to U.S. Patent Publication No. US 2012/0109035 A1, published May 3, 2012, entitled "Reversible Adhesives" and Patent Cooperation Treaty Patent Publication No. WO 2009/097561 A1, published Aug. 6, 2009, entitled "Wound Closing Compounds with Additives." The entire content of each of these applications is incorporated herein by reference, including all exhibits.

TECHNICAL FIELD

This disclosure relates to, among other things, thermo-responsive hydrogel compositions, e.g., for treating ocular perforations.

BACKGROUND

Currently, in the United States, perforations of the eye wall (i.e., punctures through the entire wall) are closed using sutures. Sutures are placed through the layers of the eye wall tissue at the apposed margins of the perforation. The margins are drawn together and held closed with knots. Typically resorbable sutures are used, and therefore the suture knots may be exposed on the ocular wall surface for an extended period of time. Sutures leave high profile knots on the exterior surface of the eye. These knots can be felt by the patient and cause discomfort, which is known to lead to eye-rubbing and subsequent infection.

Outside of the U.S., certain bioadhesives are approved for use in the eye. For example, cyanoacrylate and fibrin glue are approved for use in Europe to close scleral and/or corneal perforations. These methods are currently not approved in the United States. Moreover, fibrin glue consists of genetically stripped fibrinogen and thrombin extracted from human or animal (e.g. bovine) blood. While this material is effective and biocompatible, fibrin glues carry a risk of viral and other pathogen transmission. Cyanoacrylate (e.g. crazy glue) polymerizes in high modulus, rigid aggregates. The resulting solidified adhesive is very granular and often can feel like sand in the eye. This again can lead to discomfort and eye rubbing, which can cascade into irritation and infection. There is some evidence that unpolymerized cyanoacrylate may have some neurotoxic effects.

As noted above, both of the foregoing approaches have associated drawbacks. Provided herein are thermo-responsive polymers, hydrogel compositions, methods and devices which overcome many of the shortcomings of currently available materials and approaches for treating ocular trauma, especially under conditions requiring rapid and effective temporary treatment of ocular wounds.

SUMMARY

Generally, provided herein is a system for temporary closure of scleral perforations of the eye without the use of sutures. This system comprises a thermo-responsive polymeric gel whose adhesive and viscous properties are temperature dependent. Typically, the gel is adhesive and viscous near body temperature, and non-adhesive and non-viscous at room temperature. Also provided herein is a device for administering the polymeric gel, wherein the device comprises, e.g., components for properly manipulating and positioning the gel, controlling the temperature of the gel, and proper placement, i.e., delivery of the gel, as well as methods of making and using the polymeric gel and system.

In a first aspect, provided is a temperature-responsive hydrogel. The hydrogel comprises a poly(N-isopropylacrylamide) copolymer at a concentration of about 10 weight percent to about 60 weight percent in water, wherein the copolymer (i) is a copolymer of poly(N-isopropylacrylamide) and a second polymer that is either N-tert-butylacrylamide or butylacrylate, (ii) has a weight percent ratio of poly(N-isopropylacrylamide) to the second polymer of about 99:1 to about 50:50, and (iii) has a number average molecular weight of about 5,000 to about 5,000,000 daltons.

In one or more embodiments, the poly(N-isopropylacrylamide) copolymer is a poly(N-isopropylacrylamide):N-tert-butylacrylamide copolymer.

In one or more further embodiments, the poly(N-isopropylacrylamide) copolymer is a poly(N-isopropylacrylamide):butylacrylate copolymer.

In yet some additional embodiments, the weight percent ratio of poly(N-isopropylacrylamide) to the second polymer is selected from 99:1, 95:5, 90:10, 85:15, 80:20, 75:25, 70:30, 65:35, 60:40, 55:45 and 50:50. In some further embodiments, the weight percent ratio of poly(N-isopropylacrylamide) to the second polymer is in a range of about 95:5 to about 70:30.

In yet one or more further embodiments, the copolymer has a number average molecular weight of about 10,000 to about 3,000,000 daltons.

In yet some additional embodiments, the copolymer has a number average molecular weight of about 20,000 to about 2,000,000 daltons.

In some embodiments, the hydrogel has a copolymer concentration in water selected from the group consisting of about 10 weight percent, 15 weight percent, 20 weight percent, 25 weight percent 30 weight percent, 35 weight percent, 40 weight percent, 45 weight percent, 50 weight percent, 55 weight percent, and 60 weight percent in water.

In yet some further embodiments, the hydrogel has a lower critical solution temperature in a range of about 10° C. to about 35° C.

In some further embodiments, the poly(N-isopropylacrylamide) copolymer is a block copolymer.

In yet one or more additional embodiments, the hydrogel further comprises an excipient or additive.

In some embodiments, the hydrogel is in sterile form.

In yet further embodiments, the hydrogel has an adhesive strength in a range of about 10 mN to 10,000 mN when measured using an in vitro uniaxial adhesion test to scleral tissue at 37° C.

In some embodiments, the hydrogel comprises a bioactive agent.

In a second aspect, provided is an adhesive patch comprising a hydrogel according to any one or more of the aspects or hydrogel embodiments provided herein.

In some embodiments, the adhesive patch comprises the hydrogel deposited on a polymeric substrate. Illustrative substrates are, for example, selected from the group consisting of parylene, poly-lactic acid or co-polymeric matrices of poly-lactic and poly-glycolic acid, polyimide, liquid crystal polymer, and polydimethylsiloxane (PDMS).

In yet a further aspect, provided is a method for reversibly sealing an ocular perforation, the method comprising applying a hydrogel as provided herein to a tear in ocular tissue of a subject in an amount effective to seal the tear, wherein when exposed to a temperature above its critical solution temperature, the hydrogel becomes adhesive, and when exposed to a temperature below its critical solution temperature, the hydrogel becomes less adhesive.

In one or more embodiments related to the foregoing method, the hydrogel is maintained at a temperature below its critical solution temperature prior to said applying.

In some further embodiments of the method, the temperature of the ocular tissue is above the critical solution temperature of the hydrogel.

In yet some additional embodiments of the method, the hydrogel adheres to the tissue of the edges of the tear.

In some embodiments, the applying step comprises applying to an inner surface of an eye wall a slight excess of an amount of hydrogel effective to fill a void created by the ocular tear.

In one or more embodiments of the method, the ocular pressure is effective to press the excess hydrogel against the inner surface of the eye to thereby create an internal ocular seal.

In yet another aspect, provided is a device for delivery of a temperature responsive hydrogel, the device comprising (i) a first chamber for containing a temperature-responsive hydrogel, (ii) a second chamber at least partially surrounding the first chamber, said second chamber capable of maintaining a particular temperature or temperature range before and/or during delivery of the hydrogel, (iii) a port for delivery of the hydrogel from the first chamber to the delivery site, and (iv) a mechanism for delivery of the hydrogel from the first chamber to the delivery site.

In some embodiments of the device, the second chamber includes a cooling mechanism or material.

In some additional embodiments, the first chamber has a volume of about 0.1 mL to about 10 mL.

In one or more further embodiments, the size of the second chamber relative to the first chamber ranges from about 50:1 to about 10:1.

In some further embodiments, the second chamber further comprises a port for introduction of a coolant material.

In some further embodiments, the first chamber comprises a thermo-responsive adhesive hydrogel. In some additional embodiments, the first chamber comprises a thermo-responsive hydrogel comprising a PNIPAM-copolymer as provided herein.

In one or more additional embodiments, the second chamber comprises one or more materials effective to carry out an endothermic reaction.

In some embodiments, the one or more materials in the second chamber are sequestered from one another prior to reaction.

In some embodiments, the second chamber comprises ammonium nitrate. In an alternative embodiment, the chamber contains cooling elements that are electrically powered.

In one or more further embodiments, the device further comprises one or more tools effective to facilitate removal of a hydrogel plug from the eye.

In some additional embodiments, the device further comprises means for aspiration or irrigation of ocular tissue.

These, as well as other components, steps, features, objects, benefits, and advantages, will now become clear from a review of the following detailed description of illustrative embodiments, the accompanying drawings, and the claims.

BRIEF DESCRIPTION OF DRAWINGS

The drawings are of illustrative embodiments. They do not illustrate all embodiments. Other embodiments may be used in addition or instead. Details that may be apparent or unnecessary may be omitted to save space or for more effective illustration. Some embodiments may be practiced with additional components or steps and/or without all of the components or steps that are illustrated. When the same numeral appears in different drawings, it refers to the same or like components or steps.

DETAILED DESCRIPTION OF ILLUSTRATIVE EMBODIMENTS

Figure 1A:
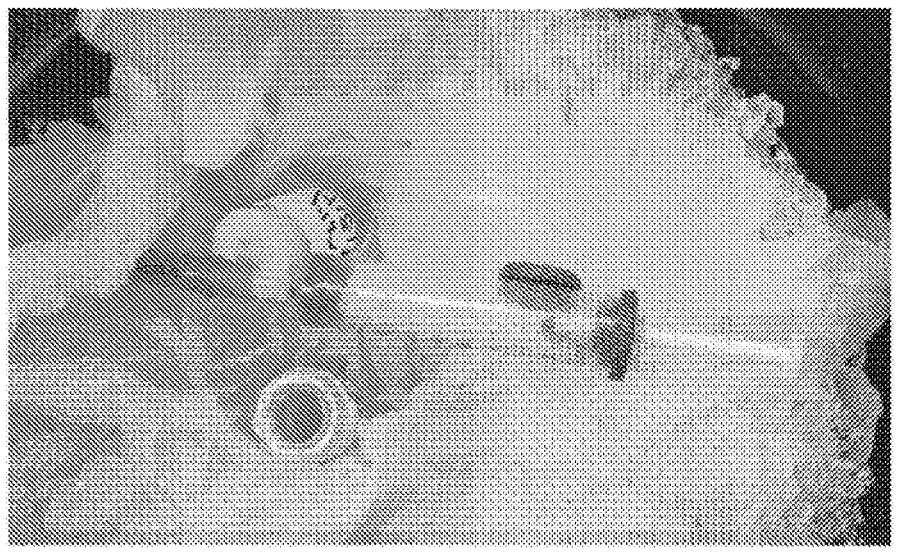
FIGS. 1A-1D provides illustrative embodiments of a device suitable for administering a reversible thermoresponsive hydrogel as provided herein. In some embodiments, the device is of a size suitable for use by a skilled practitioner, e.g., surgeon, using a single hand.

Illustrative embodiments are now discussed and illustrated. Other embodiments may be used in addition or instead. Details which may be apparent or unnecessary may be omitted to save space or for a more effective presentation. Conversely, some embodiments may be practiced without all of the details which are disclosed.

The singular forms "a," "an," and "the" include plural referents unless the context clearly dictates otherwise. Thus, for example, reference to a "water soluble polymer" includes a single water soluble polymer as well as two or more of the same or different water soluble polymers.

The term "about", particularly in reference to a given quantity, is meant to encompass deviations of plus or minus five percent.

The term "substantially" in reference to a certain feature or entity means to a significant degree or nearly completely (i.e. to a degree of 85% or greater) in reference to the feature or entity.

Where a range of values is provided, it is intended that each intervening value between the upper and lower limit of that range and any other stated or intervening value in that stated range is encompassed within the disclosure. For example, if a range of from 3 weight % to 10 weight % is described, it is intended that 3 mol %, 4 mol %, 5 mol %, 6 mol %, 7 mol %, 8 mol %, 9 mol %, and 10 mol % are also explicitly disclosed, as well as the range of values greater than or equal to 3 mol % and the range of values less than or equal to 10 mol %.

Generally, provided herein is a system for temporary closure of ocular perforations, i.e., punctures through the wall of the eye or other support structures of the eye. The system comprises, for example, a viscous polymer whose viscosity and adhesion to tissue is temperature dependent. Specifically, the viscosity and adhesion are suppressed at temperatures near room temperature (e.g. T=25° C.), while the polymer composition becomes viscous and adhesive at temperatures near physiological eye temperature (e.g. T=31° C.). Also provided herein are aspects related to, among other things: (i) an adhesive co-polymer, including a hydrogel comprising the co-polymer and its related properties; (ii) a method of placement and action by which the hydrogel composition is effective to seal an ocular perforation; and (iii) devices suitable for storing, delivering, and manipulating the adhesive during application and removal.

The instant adhesive ocular repair system (i.e., the co-polymer component, related hydrogel, delivery apparatus and related devices) is designed to temporarily occlude perforations of the eye wall (i.e. punctures through the entire thickness) and penetrations of the eye wall (i.e. insertions through a portion of the eye wall) to thereby prevent loss of intraocular pressure. Intraocular pressure is the isostatic pressure exerted by the fluid (vitreous humor) contained inside the eye. Leakage and loss of pressure can lead to retinal detachment, suprachoroidal hemorrhage, and subsequent permanent vision loss. Thus, the instant co-polymers, hydrogels, methods, and devices are useful for preventing any one of more of the foregoing conditions, among others.

Poly(N-isopropylacrylamide) Co-Polymer: Chemical Composition, Preparation and Characteristics Poly(N-isopropylacrylamide) (pNIPAM) is a temperature-responsive polymer that exhibits a reversible macro-molecular transition that demonstrates adhesive properties at body (eye) temperature and non-adhesive properties at decreased temperature. Provided herein are pNIPAM-based adhesive hydrogels effective to seal scleral wounds, among other things.

Copolymers for use in the compositions, hydrogels, methods and devices provided herein are PNIPAM-based copolymers. More specifically, provided herein is a copolymer of PNIPAM and a second polymer that is either N-tert-butylacrylamide (Formula I) or butylacrylate (Formula II). The copolymers were developed, at least in part, to provide formulations having improved adhesion to ocular tissue in comparison to formulations comprising PNIPAM alone. Generally, the copolymer has a weight percent ratio of poly(N-isopropylacrylamide) to the second polymer of about 99:1 to about 50:50. For example, the copolymer may comprise PNIPAM and the second polymer, i.e., either N-tert-butylacrylamide or butylacrylate, where the weight percentage of PNIPAM is in a range from 60 weight percent to 98 weight percent PNIPAM. The values of the subscripts x and y below will correspond to values effective to provide copolymers falling within the weight percentage ranges described above.

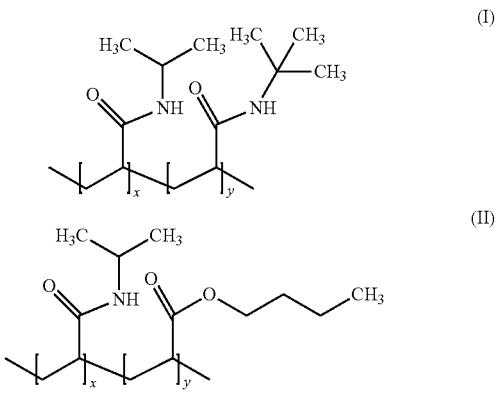

The PNIPAM-based copolymer may have a weight percent ratio of PNIPAM to the second polymer component (i.e., N-tert-butylacrylamide or butylacrylate) selected from 99:1, 95:5, 90:10, 85:15, 80:20, 75:25, 70:30, 65:35, 60:40, 55:45 and 50:50. In some embodiments, the weight percent ratio of poly(N-isopropylacrylamide) to the second polymer is about 95:5 to about 70:30. Generally, the copolymer will comprise a greater weight percentage of PNIPAM than of the second polymer, although in some embodiments, the copolymer may comprise equal percentages by weight of PNIPAM and the second polymer. Preferably, the copolymer comprises at least 50 weight percent or greater of PNIPAM, to thereby provide a copolymer having good adhesion performance, i.e., suitable for use in ocular applications.

The PNIPAM copolymer will typically possess a number average molecular weight of about 5,000 to about 5,000,000 daltons, or from about 10,000 to about 3,000,000 daltons, or from about 20,000 to about 2,000,000 daltons. Illustrative number average molecular weights include, for example, 5 kD, 10 kD, 15 kD, 20 kD, 25 kD, 30 kD, 40 kD, 50 kD, 60 kD, 70 kD, 80 kD, 90 kD, 100 kD, 200 kD, 300 kD, 400 kD, 500 kD, 600 kD, 700 kD, 800 kD, 900 kD, 1,000 kD, 1500 kD and 2000 kD, including all ranges between any two of the foregoing values.

Copolymers as provided herein can be prepared using known methods and available starting materials. See, e.g., G. G. Chen, AS Hoffman, Nature 1995-01-05, and A Gutowska, et al., Journal of Biomedical Materials Research 1995-07-01. An exemplary copolymer synthesis is provided herein as Example 1.

The instant PNIPAM:n-tert butylacrylamide and PNIPAM:butylacrylate co-polymers have been developed to provide thermoresponsive hydrogel compositions having improved adhesion performance over hydrogels comprising PNIPAM as a single thermoresponsive polymer component. The instant copolymers were designed to provide polymers having a critical solution temperature that is lower than that of PNIPAM-alone. Introduction of a second copolymer component was effective to introduce a higher level of hydrophobicity into the hydrogel composition at body temperature, to thereby provide a PNIPAM copolymer having a balance of features, which when comprised within the instant hydrogels, are suitable for treating ocular tears, as well as for treating other ocular injuries or conditions.

Generally, the copolymers are block copolymers having properties particularly well suited for ocular applications. Representative hydrogels comprising the PNIPAM copolymers may comprise one or more of the following features:

TABLE 1

|  | PNIPAM:N-tert Butylacrylamide Co-Polymer | PNIPAM:Butylacrylate Co-Polymer |
|---|---|---|
| Preferred Chemical Formula: | $(C_6H_{11}NO)_x:(C_7H_{13}NO)_y$ | $(C_6H_{11}NO)_x:(C_7H_{12}O_2)_y$ |
| Co-Polymer wt % Ratio: | [99%:1%] to [50%:50%] | [99%:1%] to [50%:50%] |
| Preferred Number Average Molecular Weight Range: | 5,000 to 5,000,000 (<800,000) | 5,000 to 5,000,000 (<800,000) |
| Preferred Percent Aqueous Solution Range | 10% to 60 wt % solids | 10% to 60% wt % solids |

The performance of the subject adhesive co-polymers is dependent, for example, on the lower critical solution temperature (LCST) of the co-polymer. The LCST is the temperature below which the solution becomes hydrophilic and less adhesive, and above which it becomes more hydrophobic and adhesive. Table 2 provides representative LCST ranges for the instant PNIPAM-based copolymers. Preferred polymers are those that become more viscous upon application to the environment of the eye. For instance, the copolymer may possess a LCST of 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., or 37° C.

TABLE 2

|  | PNIPAM:N-tert Butylacrylamide Co-Polymer | PNIPAM:Butylacrylate Co-Polymer |
|---|---|---|
| Desired LCST Range (° C.): | 10° C. to 35° C. | 10° C. to 35° C. |

Hydrogels

The instant hydrogels typically comprise from about 10 wt % about 60 wt % PNIPAM copolymer in water. Illustrative copolymer concentrations in water include, for example, 10 weight percent, or 15 weight percent, or about 20 weight percent, or about 25 weight percent, or about 30 weight percent, or about 35 weight percent, or about 40 weight percent, or about 45 weight percent, or about 50 weight percent, or about 55 weight percent, or about 60 weight percent in water.

The hydrogel may also contain one or more excipients, stabilizers, additives or the like. The instant hydrogels may also comprise a bioactive agent, a diagnostic agent, a cosmetic agent, colorant (to enhance visualization), or any other agent suitable for delivery to the eye. For example, in one or more embodiments, the hydrogel may comprise a therapeutically effective amount of a bioactive agent. Representative active agents include but are not limited to, for example, antibiotics, anti-inflammatory agents, chemotherapeutic agents, steroids, and immunosuppressants.

Generally, the instant hydrogels possess several advantageous properties. For example, the instant hydrogels generally possess one or more of the following features. In some embodiments, the hydrogel is non-cytotoxic. In some other embodiments, the hydrogel is bioinert or biocompatible. In some further embodiments, the hydrogel is biodegradable. In yet some further embodiments, the hydrogel is inherently antibacterial.

The instant hydrogels will typically possess physical properties such that they can be tailored for use in an unsupported, fluid form or can be used in a more structured patch form (i.e., where the hydrogel itself provides its own mechanical structure and shape); alternatively, the hydrogel may be applied to a substrate whereby the hydrogel provides sealing/adhesive properties and the substrate provides mechanical support, shape and structure.

Additionally, the instant hydrogels are typically adhesive and viscous at body (e.g., eye) temperature (e.g., temperatures from about 30° C. to about 37° C.) or higher, or reach their final desired state at body temperature or higher. Favorably, the instant hydrogels can also be manipulated, positioned, and re-positioned at temperatures below body temperature.

In some embodiments, the hydrogel integrates chemistries that facilitate identification of fluid leakage in the eye.

Patches

Figure 4:
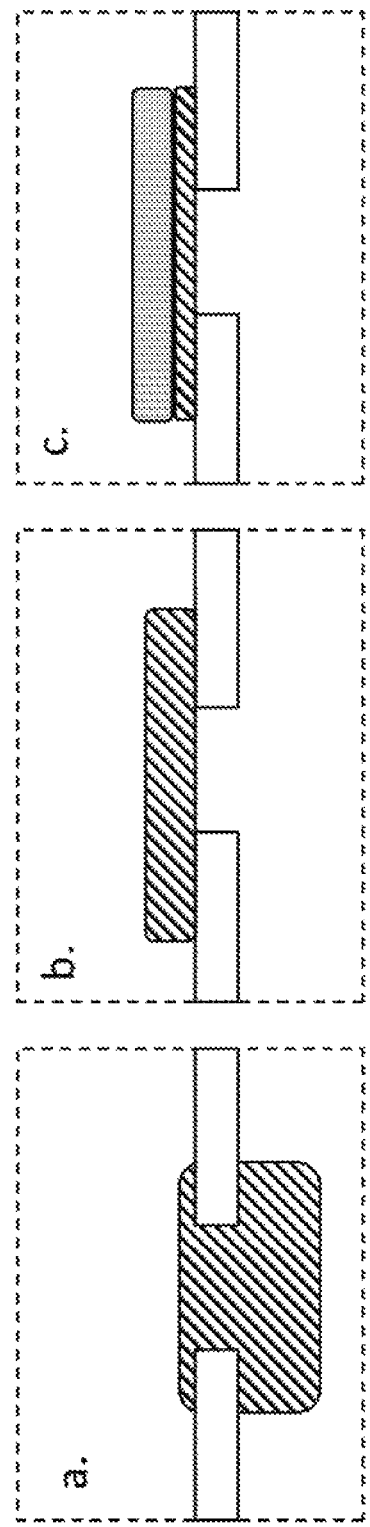
FIG. 4 is a schematic illustrating various patch styles including (a) an unsupported fluid hydrogel, (b) an unsupported patch hydrogel and (c) a supported patch hydrogel.

As described above, the hydrogel may be provided in supported form, that is to say, deposited on a substrate. In one or more embodiments, the substrate is a flexible substrate also referred to herein as a backing layer or support. FIG. 4 provides schematic illustrations of various patch styles including (a) an unsupported fluid hydrogel (diagonal lines, e.g., filling an ocular void or tear), (b) an unsupported patch hydrogel (e.g., placed over an ocular tear or void) and (c) a supported patch hydrogel, where the hydrogel is situated upon a support. In one or more embodiments as illustrated in FIG. 4(a), the hydrogel is an unsupported fluid material which plugs the penetrating injury. In one or more embodiments as shown in FIG. 4(b), the hydrogel is a more structurally defined patch placed over an ocular injury. In such embodiments, the patch uses its adhesive properties to maintain a seal around the margins of the injury. Additionally, the mechanical integrity of the hydrogel is greater than in its fluid form, and can thus hold the margins of the injury together. In one or more embodiments as provided in FIG. 4(c) the hydrogel is fixed onto a supportive substrate. The substrate provides mechanical integrity and contributes to sealing performance. The hydrogel in this embodiment serves to form an adhesive seal between the substrate and the tissue surrounding the trauma.

Figure 3:
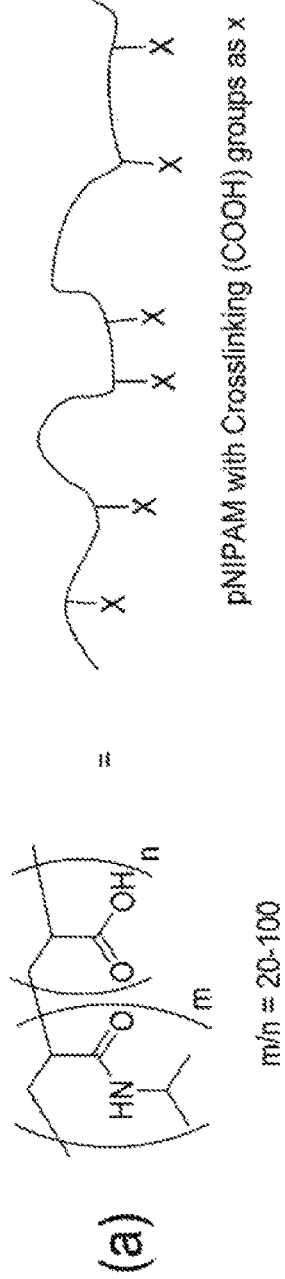
FIG. 3 is a schematic illustrating modification of a PNIPAM copolymer with crosslinkable groups abbreviated as "X" (a), and crosslinking of the copolymer (b) to provide a crosslinked matrix that may also be crosslinked to a support. The crosslinking reaction leads conversion of x to y, with crosslinks illustrated by bold lines.
Figure 3:
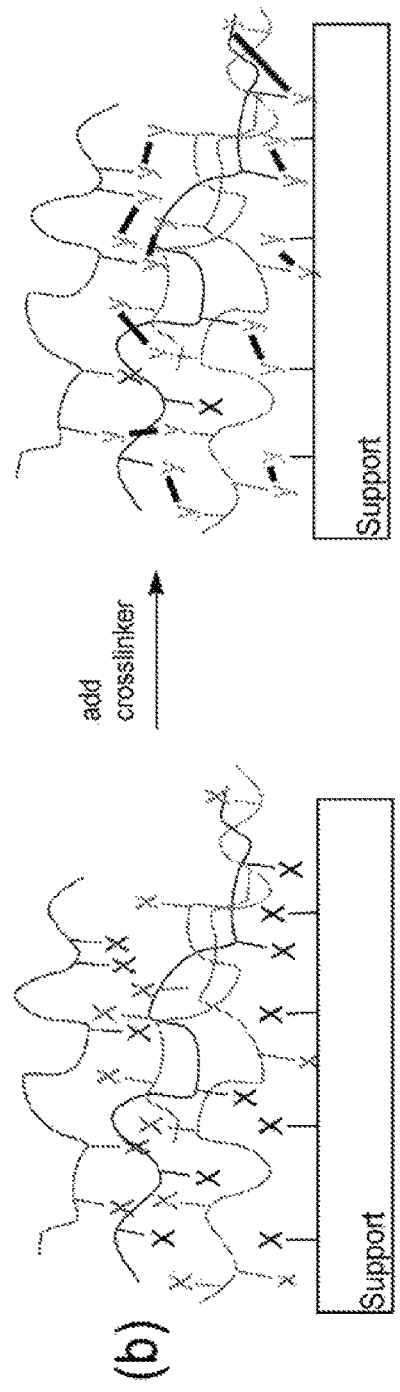

In one or more embodiments, a patch is prepared by utilizing pNIPAM copolymers further modified with suitable crosslinkable functionalities or X-groups; such crosslinking groups are well known in the art. For example, the copolymer may be modified to comprise crosslinking groups at from about 1-5% of the sites on the polymer chain, indicated by "X" in FIG. 3. By virtue of adding crosslinkable groups, X, the polymer chains together can provide the pNIPAM copolymer as a single, interconnected mass (FIG. 3, (b)) by virtue of addition of a suitable crosslinker. The crosslinks are illustrated by bold lines and conversion of the X groups to "y" groups. For example, if the X-groups are COOH, they can be crosslinked with alkyl-diamines to form an interconnected network that spans the entire polymer film. Moreover, if the substrate is decorated with the same. X-groups as the polymer, crosslinking will take place between the polymer and substrate as well, Chemistries for modifying substrate surfaces with functional groups suitable for covalent attachment are well known.

In some embodiments, the PNIPAM copolymer is deposited on a substrate. Exemplary substrates include parylene, poly-lactic acid, polyimide, and polydimethylsiloxane, among others. A preferred substrate material is parylene. Parylene may be surface modified with carboxyl, amino, hydroxyl, alkyl-halide and other suitable crosslinkable groups using known chemistries. See, e.g., Wahjudi, J. H., et al., *Journal of Biomedical Materials Research*, Part A, 2009, 89A (1), 206-214. In one or more embodiments, the crosslinking reaction that is effective to stabilize the pNIPAM-copolymer film may also be employed to anchor it to a support surface. An pNIPAM-copolymer film having an initial thickness can be made arbitrarily thicker by addition of a crosslinker dissolved in the polymer film. Heating or irradiating the film can promote a crosslinking reaction.

Illustrative crosslinking chemistries include, for example, use of a PNIPAM copolymer comprising a small number of 2-hydroxyethylacrylate groups, which can then be efficiently cross-linked with tartaric acid. The foregoing copolymer can also be cross-linked with other poly-functional carboxylic acids (malic, citric, malonic, succinic, glutaric adipic acid) using ester- or etherification or N,N'-methylenebisacrylamide. Diamines such as triethylenetetramine may be used to crosslink PNIPAM copolymers functionalized with monomers containing an active ester group such as N-hydroxysuccinimide (NHS).

In some embodiments, the support is at least partially flexible to allow for delivery at sites that are not flat. In some embodiments, the backing layer is sufficiently flexible to conform to a delivery site such as the eye. In some embodiments, the patch includes an optional release liner that covers the adhesive hydrogel prior to application at the delivery site. In preferable embodiments, the release liner is impermeable and/or non-reactive with the adhesive hydrogel.

Device

In yet another aspect, provided herein is a device for storing, manipulating and delivery of the instant hydrogels to ocular tissue. In one or more embodiments, the device may also be used for heating saline infusions. In some embodiments, the hydrogel is delivered to its desired target site with minimal release of excess copolymer.

In some embodiments, provided is a device that is capable of reducing the temperature of the hydrogel. In one or more further embodiments, the device is also capable of facilitating co-polymer detachment from tissue. In yet one or more further embodiments, the device additionally comprises manipulation features (e.g. stylus, probe, forceps, or scalpel, etc.) to assist in manipulating the hydrogel plug to facilitate removal. In yet some further embodiments, the device may include aspiration and/or irrigation capabilities to facilitate removal of the co-polymer.

Thus, in one aspect, a device for maintaining a desired temperature and for delivery of a reversibly thermally-responsive adhesive hydrogel is described herein. In general, the device includes a first chamber for containing the adhesive hydrogel and a second chamber at least partially surrounding the first chamber for holding the adhesive hydrogel at a particular temperature or temperature range before and/or during delivery of the adhesive hydrogel. The device also includes a port, opening or other structure for delivery of the adhesive hydrogel from the first chamber to the delivery site. Finally, the device includes structure and/or a mechanism for delivery of the adhesive hydrogel from the first chamber to an intended delivery site.

In one exemplary embodiment, as shown in FIGS. 1A-1D, the device 100 includes a first chamber 102 that is at least partially positioned within a second chamber 104. In the embodiments as shown in FIGS. 1A-1D, the first chamber is nested within the second chamber. The first and second chambers are operatively connected in a suitable manner such that the first chamber is at least partially maintained within the second chamber. In the embodiments shown in FIGS. 1A-1C, the first and second chambers are connected at a first end 106. It will be appreciated that in some embodiments the first and second chamber may be formed of separate pieces that are mechanically attached or adhered. In other embodiments, the first and second chambers may be formed of a single piece. In some embodiments, the first and second chambers are formed of separate pieces that are adhered using a suitable adhesive. Suitable adhesives are known in the art and may be determined by requirements of the materials used for the first and/or second chambers. The size and/or volume of the first and second chambers may be selected as necessary for ease of use and/or the requirements of the delivery site. For example, in some embodiments, the device may be intended for use by one hand of a user. In this embodiment, the width of the second chamber and length of the device may be determined by the needs of holding the device. In some non-limiting embodiments, the device has a total length of up to about 6-10", about 6-9", about 6-8" or about 6-7". Similarly, the volume of the first and/or second chambers may be sized to hold a desired amount of material. In some embodiments, the first chamber is sized to contain at least about 0.25-5 mL or up to about 5 mL of the adhesive hydrogel. In other embodiments, the first chamber is sized to contain at least about 0.5-5 mL, about 1-5 mL, about 1.5-5 mL, about 2-5 mL, about 2.5-5 mL, about 3-5 mL, or about 4-5 mL.

The device further includes an opening, delivery port, or nozzle 108 for delivery of the adhesive hydrogel to the treatment area. The discussion hereafter is with reference to a nozzle, although it will be appreciated that the discussion is applicable to other embodiments of a delivery portion of the device as appropriate. As seen in FIG. 1C, the nozzle is connected to the first chamber such that the adhesive hydrogel may flow from the first chamber, through the nozzle and to a delivery site. The length and diameter of the nozzle may be any suitable dimension as required for the delivery site. In some embodiments, at least the end of the nozzle has a gauge ranging from 10 gauge through 24 gauge in tube bore.

The device further includes a delivery mechanism 114 that effects delivery of the adhesive hydrogel from the first chamber 120, through the nozzle 108 and to the delivery site. FIG. 1D depicts an embodiment where the delivery mechanism is a plunger-type mechanism 118. Movement of the plunger in the direction of arrow 120 pushes the adhesive hydrogel through the first chamber to the delivery site. In the embodiment as shown in these figures, the plunger is manually operated. However, it will be appreciated that the delivery mechanism may be operated by other means as known in the art including, but not limited to, remote operation using a processor. Preferably, the delivery mechanism provides a seal with the first chamber during storage and during delivery so that the adhesive hydrogel does not exit the first chamber at the opposite end from the nozzle. The nozzle may be formed of any suitable material known in the art that is suitable for delivery of the adhesive hydrogel. In embodiments, the material of the nozzle is selected from a material that is minimally thermally conductive. A material that is minimally thermally conductive prevents or minimizes an increase in temperature of the nozzle from contact with the delivery site. In some embodiments, the nozzle is formed from a plastic such as that used for IV catheters.

In some embodiments, the second chamber includes a cooling mechanism or material as described herein. In some embodiments, the second chamber includes an opening or port 110 allowing access to the second chamber. In embodiments, the cooling mechanism may be pre-loaded or the cooling mechanism may be a continuous cooling mechanism. A continuous cooling mechanism may include a recirculating coolant and means for cooling the coolant during circulation. The size of the second chamber may be any suitable size as required to contain the recirculating cooling system or, alternatively, to contain a suitable amount of coolant material. In some embodiments, the second chamber should be sized to contain an amount of coolant material that cools the adhesive hydrogel in about 3-5 seconds. In other embodiments, the second chamber should be sized to contain an amount of coolant material sufficient to maintain the temperature of the first chamber at about 0-10° C. for at least about 10 minutes. As one example, where the first chamber contains about 0.5 mL of an adhesive hydrogel, the second chamber should be sized to contain about 7-10 g of a cooling material such as ammonium nitrate and about 5-20 mL of water.

In some embodiments where the cooling mechanism requires addition of a reactant (e.g. addition of water to ammonium nitrate or vice versa), the reactant (or additional reactant) may be added to the second chamber through the port. The port may be open or resealable. In some embodiments, a plug 112 is used to seal the port. The plug may be removable and/or may allow for introduction of a material through the plug. In some embodiments, the plug is formed of a material that can be pierced to allow a reactant to be added (or removed) from the second chamber. In one non-limiting embodiment, the plug is a rubber plug that may be pierced for addition or removal of a reactant. In some embodiments, the second chamber is air-tight and/or liquid tight when the port is sealed by a plug.

Further in reference to the embodiment provided in FIG. 1D, the device includes an internal hydrogel reservoir for storing the hydrogel prior to its use, which is surrounded by a jacketing reservoir/space designed to contain a system for regulating the temperature of the hydrogel reservoir. This jacket may be a volume space for filling with endothermic reactants or a cavity filled with cooling elements (e.g. electrical elements). In embodiments in which chemical reactions are used to cool the system, an access port may be required to introduce reactants. Examples of endothermic reactions that may be employed include ammonium nitrate and water; urea and water; and barium hydroxide, ammonium chloride and water.

One end of the long axis of the device may be fitted with a nozzle/needle for releasing/deploying the hydrogel from the reservoir into the target site. This tip should be thermally insulating either by design or materials selection or both. Access from the reservoir to the nozzle may be controlled by a gating mechanism, e.g., to prevent leakage or premature release of hydrogel and/or to control release during deployment. In some embodiments, the hydrogel may be driven out of the reservoir using a plunger type mechanism. This mechanism may be actuated manually by applying pressure to the plunger end by the user, or alternatively, may be automated by using a driver type mechanism, e.g. a spring loading mechanism, or a servo motor, or other subsystem.

FIG. 1A is an image of an embodiment of a device for delivering a thermos-reversible hydrogel. In the embodiment illustrated, a 1 mL syringe serves as a reservoir for the hydrogel, while a 10 mL syringe serves as a jacketing reservoir, e.g., for cooling the hydrogel. In the exemplary embodiment, the jacketing reservoir is filled with ammonium nitrate. The ammonium nitrate can be placed into the reservoir via a loading port accessible for example, via a plug on the external cylindrical wall of the jacket as shown. In this embodiment, a sterile plastic catheter tip (covered with a cap at left) is used to transfer the hydrogel from the reservoir to the target tissue site. The entire unit may, if desired, be stored over ice prior to use to further accelerate cooling of the hydrogel.

Figure 1B:
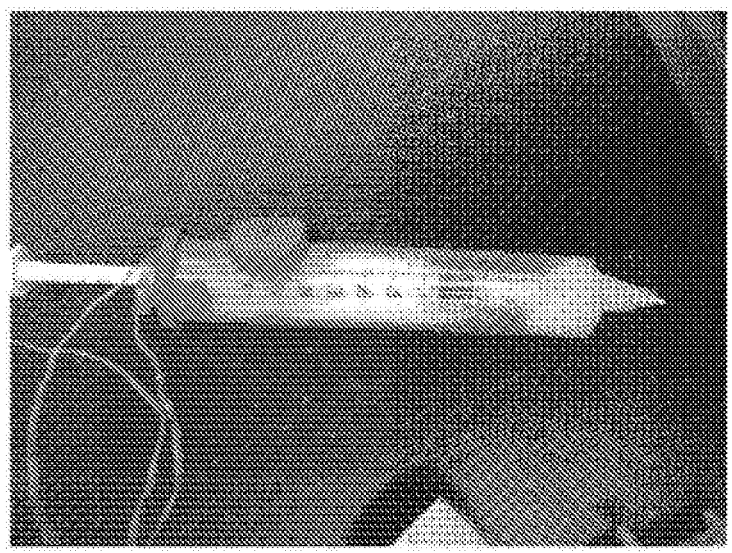
Figure 1C:
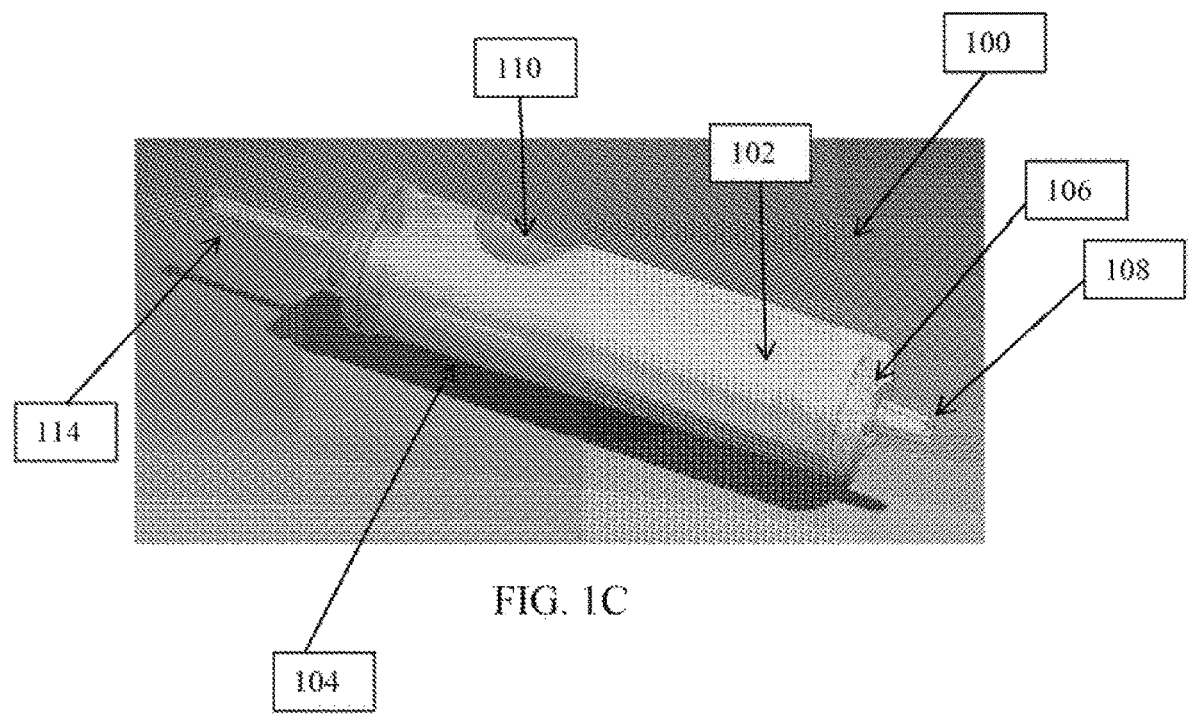
Figure 1D:
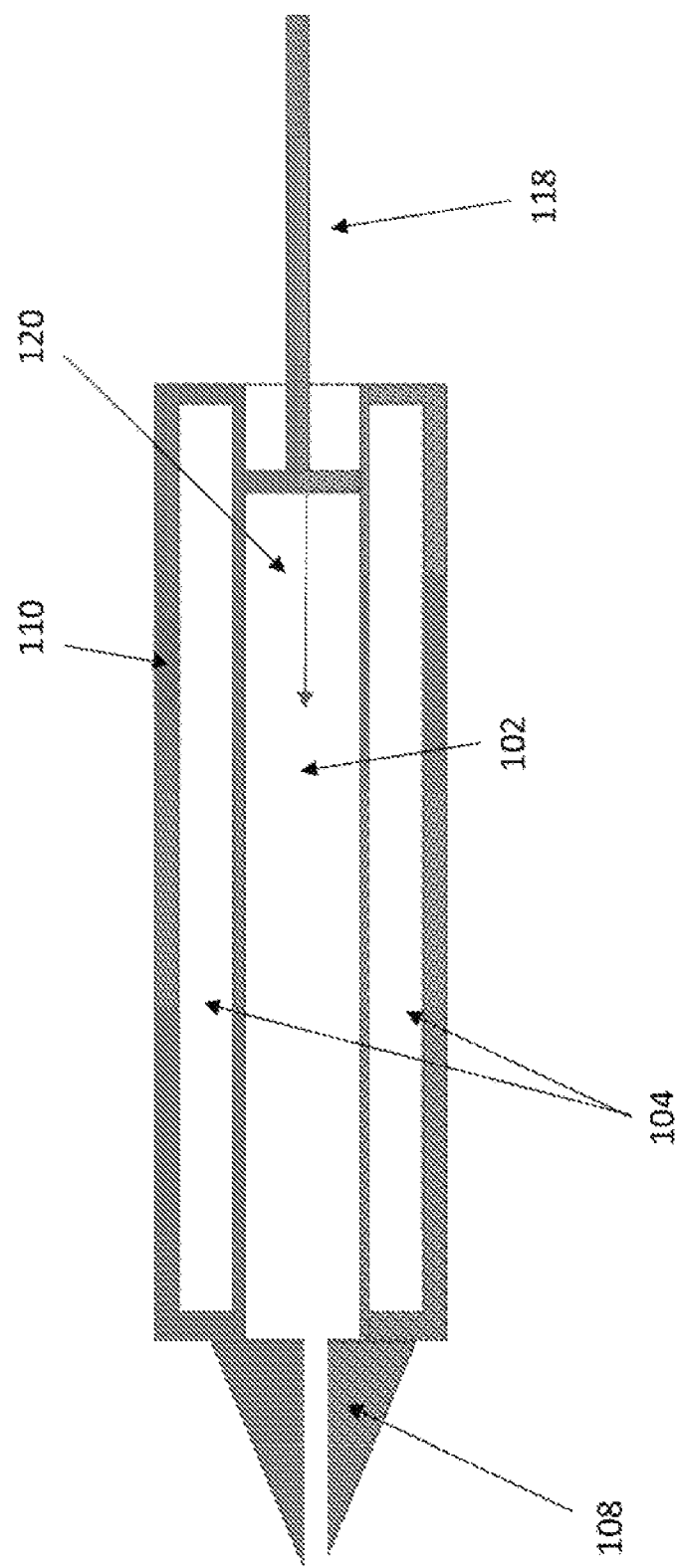

FIG. 1B illustrates an embodiment of the device wherein the device comprises integrated temperature sensors for monitoring the temperature inside the jacket and inside the hydrogel reservoir. In one or more embodiment, the device may comprise one or more temperature sensors for monitoring the temperature inside the jacket, or inside the hydrogel reservoir, or at both locations.

The device, and each separate piece of the device, may be formed of any suitable material including, but not limited to, metals, polymers, and plastic. The choice of material may be guided by whether or not the device is reusable or disposable, which typically requires the use of more cost effective materials.

Although, the devices as shown in FIGS. 1A-1D are cylindrical, it will be appreciated that the device may have any suitable shape as needed. The device may further include grips and/or specific shapes to enhance holding of the device. For example, where the device is designed to use similar to a pen, the device may include rubber grips or areas positioned on the second chamber near the nozzle to enhance grip. In other embodiments, the device may be shaped or ergonomically designed to be used manually.

The device may further include sensors such as temperature sensors that monitor the temperature of the first chamber, second chamber and/or the nozzle. FIG. 1B shows temperature sensor 116 to monitor the temperature of the first chamber.

Figure 2:
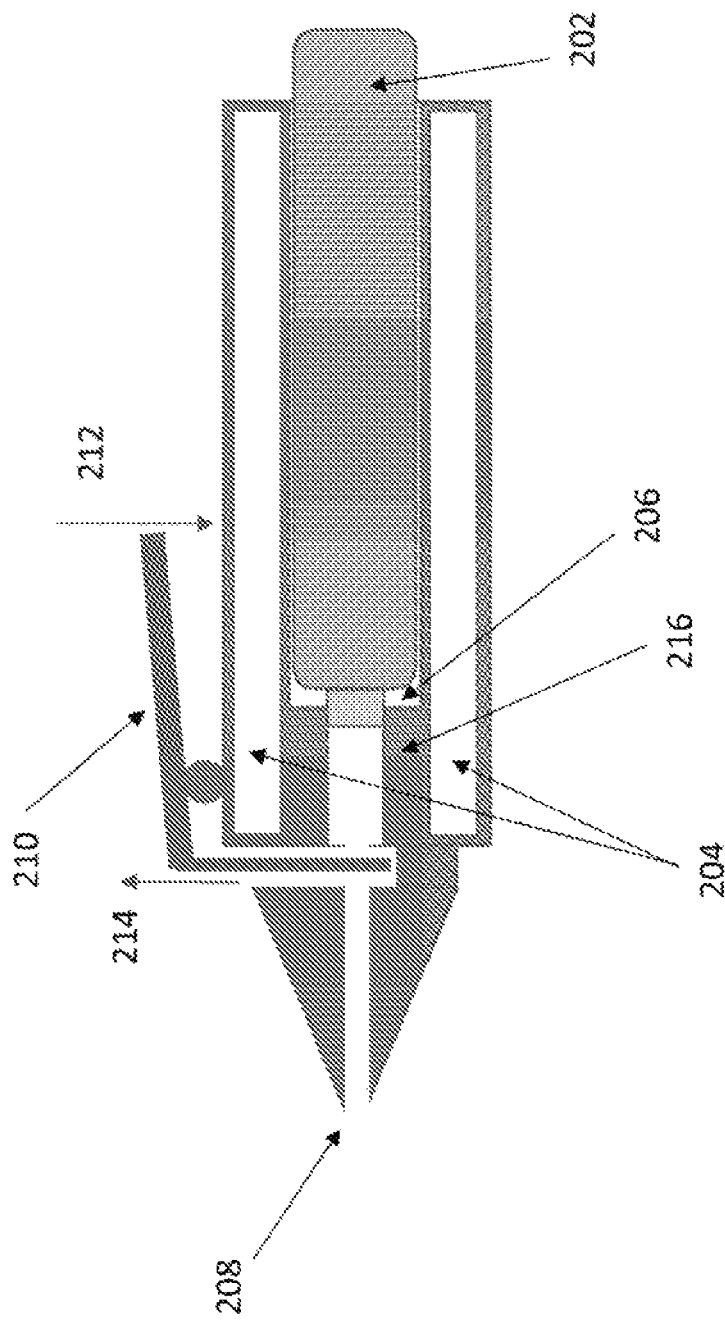
FIG. 2 provides an embodiment of a device for administering a thermally-responsive hydrogel using a pressure cartridge for storing and maintaining the hydrogel at a temperature suitable for manipulation of the gel.

In some embodiments, rather than requiring storage at cool temperatures, the hydrogel may be stored under pressure. In some embodiments, the adhesive hydrogel is stored under pressure in a suitable cartridge. For these embodiments, the delivery device may be configured to deliver the adhesive hydrogel from a pressure cartridge. One suitable embodiment using a pressure cartridge is shown in FIG. 2. In these embodiments, the cartridge 202 comprising the adhesive hydrogel under pressure is at least partially insertable into a cooling chamber 204. As seen in FIG. 2, the cooling chamber 204 has an open section for insertion of the cartridge 202. The device may include a holder 216 for the maintaining the cartridge within the cooling chamber. The holder may include means for retaining the cartridge including, but not limited to, a threaded area for mating with the cartridge or a narrowed area that at least a portion of the cartridge may be inserted into for retention of the cartridge. In one embodiment, the cartridge is in an open configuration while in the holder.

The device further includes an actuator for releasing the adhesive hydrogel from the cartridge to the delivery site. One embodiment of a mechanical actuator 210 is shown in FIG. 2. In this embodiment, the cartridge 202 is inserted into and retained by the holder 216. The device may further include a piercing member that pierces or opens the cartridge during insertion of the cartridge into the holder. The actuator in a first position seals the cartridge or holder to maintain the pressure of the cartridge and prevent delivery of the adhesive hydrogel. Movement of the actuator to a second position allows release of the pressure and the adhesive hydrogel from the cartridge, through the nozzle 208 and to the delivery site. In one embodiment, the actuator includes a handle portion, a hinged portion, and a sealing portion. Movement of the handle portion in a direction as shown by arrow 212 results in movement of the sealing portion away from the cartridge and holder (see arrow 214), resulting in delivery of the adhesive hydrogel.

In the embodiment provided in FIG. 2, the pressurized container may allow for longer storage of the hydrogel and hydrogel release without a need for mechanical actuators to drive release. A gating mechanism is provided to control release of the pressurized hydrogel. As described above, the release port/injector tip is preferably fabricated from a thermally insulating material or is designed in such a manner as to minimize thermal conduction from the external environment to the lumen of the injector tip.

In one or more embodiments, the device allows for easy transportation, deployment and manipulation of a thermo-responsive, reversible adhesive for placement in or on a targeted site.

In one or more additional embodiments, provided is a device comprising a hydrogel reservoir, a jacketing reservoir surrounding the hydrogel reservoir which may be used to provide thermal control of the hydrogel reservoir contents, a dispenser tip from which the hydrogel is deployed from the reservoir to a targeted area, a gating mechanism which allows controlled of release of the hydrogel from the tip, and an actuation system which provides a driving force to move the hydrogel from the reservoir out through the tip.

In yet some further embodiments of a device, the actuation system is driven by a mechanical mechanism, or is driven by an induced pressure, or via an electro-mechanical system or other method for displacing hydrogel from the reservoir towards the outlet dispenser tip.

In some embodiments, the device may be modular with interchangeable parts, or alternatively, may be comprised of a single working unit.

In some embodiments, the device comprises parts which may come into a sterile field for operation, and that can be sterilized or are sterile.

In one or more embodiments, the device is reusable. Alternatively, the device may be for single use.

In some embodiments, the device is capable of measuring the amount of hydrogel deployed.

In some embodiments, the device can report/provide temperatures of the hydrogel inside the reservoir, or can provide targeted deployment site surface temperature, or both.

In a preferred embodiment, the device can be operated by a single user using a single hand; in an alternative embodiment, the device can by operated by a single user using both hands. In some further embodiments, the device can be operated using foot or other body-controlled actuators.

The device may allow the hydrogel to be stored in a usable condition for prolonged periods of time regardless of external environmental conditions (high temperature, low temperature, etc.). In some embodiments, the device is relatively lightweight, allowing for easy manipulation of the hydrogel during implantation.

In some embodiments, the device comprises a system for rapidly cooling and maintaining a cold hydrogel temperature for a period of time sufficient to allow proper adhesive deployment; the system can be electrically driven or provided by virtue of an endothermic reaction driven, or via another mechanism.

In some embodiments, the device is capable of delivery of an amount of hydrogel sufficient for carrying out a desired procedure without requiring refilling. The volume may be from about 1 mL of adhesive hydrogel to as much as 50 mL of hydrogel.

In some embodiments, the device complies with specifications which meet military medical requirements above and beyond normal specifications; examples include improved packaging, enhanced transportation testing specifications, and improved thermal stability, to name a few.

The device will generally, in one or more embodiments, include a dispenser, cannula, or needle that is thermally insulated to minimize thermal energy transmission from the external environment to the lumen of the tube to prevent premature hydrogel fixation.

In one or more further embodiments, the device can be sterilized without compromising its ability to operate.

In one or more further embodiments, the device allows for the hydrogel to be transferred from the reservoir to the dispenser for deployment in a sterile field.

In some further embodiments, the device is a plug-in style device which may be electrically wired, for example, for use in a surgical theater where full facilities may be present and a larger device could be stored, maintained and operated.

In one or more additional embodiments, the device incorporates plug in electronics to drive cooling or actuation for hydrogel release.

It will be appreciated that in some embodiments, the device may be useful for delivery of other thermosensitive materials.

Methods of Use

In one or more embodiments, the instant hydrogel is a free flowing thermo-reversible hydrogel adhesive that is effective to occlude penetrating injuries through tissue by placing a bolus of the hydrogel across the margins of the penetration to provide a mechanical occlusion. In some embodiments, by virtue of becoming viscous at an elevated temperature such as body temperature or above, the hydrogel is effective to provide a physical or mechanical occlusion to the opening in the tissue.

In one or more further embodiments, a method is provided for adhering the hydrogel to an ocular tissue surface to thereby provide a seal to separate two regions which were previously connected by a penetration through the tissue.

In one or more additional embodiments, a method for delivering a hydrogel to an ocular tear is provided. For example, the hydrogel may first be being cooled down below its lower critical solution temperature (LCST), followed by application to an ocular tissue site. By cooling the hydrogel below its LCST, the hydrogel can be more readily manipulated and deployed, by virtue of its lower viscosity. Once in place, the hydrogel is allowed to raise above its LCST to thereby fix the hydrogel into position, via either adhesive fixation or mechanical fixation, or via another suitable method of immobilization. Typically, the instant hydrogels and methods are useful for closing linear perforation of about 3 cm or less, or of about 2 cm or less.

In yet an additional method, the reversibly adhesive hydrogel is applied as either a supported or unsupported patch over an area of compromised (cut, missing, penetrated, etc.) tissue to temporarily reestablish continuity of the tissue.

In one or more further embodiments, a method of applying a hydrogel is provided wherein temperature is employed to reversibly control the adhesion/occlusion characteristics of the hydrogel for a therapeutic effect. For example, heat is used to allow the hydrogel to become fixed upon application to a target site, and cooling is used to release the hydrogel from the target site at some point following its application, e.g., after it is no longer needed.

In yet one or more additional embodiments, the hydrogel may be released from its target site, e.g., ocular tissue, by reducing its local temperature, for example by applying a small stream of iced water to the hydrogel directly via an irrigation tool.

In one or more further embodiments, provided is a method to occlude penetrating injuries to tissues, for example, in the case of a penetrating injury to the wall of the eye (the sclera). Generally, the injury is first located and characterized to determine the likelihood that the hydrogel may be effective in addressing the problem. If application is via a device, device may be prepared for use (e.g. unpackaged, sterilized, etc.), and the hydrogel then allowed to reach its desired working temperature, e.g. cooled. Once at its working temperature, the hydrogel can be administered to the injury site. Once in place, the hydrogel may be afforded time to raise in temperature and transition above its LCST. Once the hydrogel becomes more viscous, excess material on the exterior of the placement site may be excised, e.g. using shears or a blade.

Thus, the instant hydrogels can be effective to seal an ocular tear by (1) filling a void created by the perforation with a mass of co-polymer, (2) adhering to the tissue of the margins (edges) of the perforation, and (3) injecting a slight excess of polymer at the inner surface of the eye wall, the ocular pressure presses excess polymer against the inner surface, creating an internal seal. Thus, the hydrogel once applied creates a "plug" that fills and self-seals the ocular perforation. Once in place, excess polymer on the exterior surface of the eye can be shaved away with a scalpel or other cutting device to create an ultra-low profile on the surface of the eye, thus minimizing discomfort.

In instances in which posterior segment surgery requires a procedure called a vitrectomy, in which the vitreous—a jelly like biological material filling the larger posterior chamber of the eye—is removed and substituted with room temperature saline via infusion, if the saline is at room temperature, this may delay or inhibit transition of the adhesive hydrogel from non-viscous to viscous.

The hydrogel, devices and methods provided herein are well suited to address problems associated with penetrating injuries to the eye. The eye consists of a firm, walled structure (the sclera) that creates the spherical boundaries of the eye. Inside of the sclera, the majority of the volume is filled with a jelly-like, transparent fluid, the vitreous humor. The interior, posterior wall of the eye is lined with the retina, the sensory tissue which is responsible for converting images observed by the individual into neural signals which are then transmitted to the brain via the optic nerve. The interior of the eye is under pressure with respect to the exterior of the eye, created by continuous secretion of aqueous humor in the anterior segment of the eye.

A penetrating injury to the wall of the eye disrupts the continuity of the sclera, and more importantly, can compromise the internal pressure of the eye. This can cause the internal contents of the eye, e.g. the vitreous humor, to release from the eye, and can potentially lead to prolapse of the spherical structure. The thin layer of retinal tissue on the posterior wall may detach as a result of the drop in pressure and loss of shape. Sealing the penetrating injury stops further release of vitreous humor and allows the aqueous humor production to re-establish internal pressure. In one or more preferred embodiments, a method of administering a hydrogel is provided in which the penetrating injury is completely sealed around its margins, whether the margins are regular or irregular.

In some embodiments, a hydrogel patch is provided in a fluid, unsupported form. For example, the hydrogel may be injected from a suitable device through the site of the penetrating injury. The injection may be conducted to allow a bolus of hydrogel material to deposit in the interior chamber of the eye. Preferably, the internal bolus has a perimeter larger than the perimeter of the margins of the injury, to thereby allow proper coverage and sealing. Delivery of the hydrogel may then continue through the margin plane. Delivery of the hydrogel continues over the exterior of the plane of the injury, e.g., to thereby form an exterior cap over the injury. Generally, the hydrogel is then allowed time to cure. Thermal energy may be applied, for example in the form of a heat lamp, to help accelerate the fixation. In some embodiments, the hydrogel forms a rivet like structure which improves its ability to seal the penetration as the internal pressure in the eye builds. At an appropriate time, the hydrogel plug may be removed, e.g., by applying cold water. Upon application of cold water, the polymer is rehydrated to its fluid form to thereby facilitate its removal.

Generally, the hydrogel is used for temporary occlusion/sealing of ocular perforations. Illustrative temporary time periods include periods of less than about 30 days. For example, the hydrogel plug may be removed within about 30 days following administration, or within about 20 days following administration, or within about 15 days following administration. Typically, the hydrogel plug will remain in its deployed position for no more than about 7-10 days.

Unlike other adhesives used in the body (e.g., cyanoacrylate, fibrin glue), the adhesive nature of the PNIPAM-copolymer based hydrogel is easily reversed by simply lowering the temperature. Therefore, closure of ocular perforations can be performed temporarily, then reopened easily. This is convenient in cases where multi-stage surgeries may be required to repair the eye. Rather than place sutures in the eye between procedures—a process which can cause additional damage and create discomfort for the patient—this temporary adhesive allows easy re-entry.

Advantages of the instant compositions, methods and devices provided herein include the ability to close an ocular perforation while maintaining a low profile on the eye surface, thereby eliminating frictional discomfort. Another significant advantage is the reversibility of adhesion. For example, in combat medicine, casualties presenting with ocular trauma are typically first stabilized at surgical hospitals (FSH) or combat service hospitals (CSH), until they can be air lifted to base hospitals with better equipment and more specialized medical personnel that can perform more elaborate procedures. In the event of ocular trauma in the battlefield, these casualties' eyes may be debrided and sealed to prevent complete loss of the eye, but reattachment of retina or other reconstructive procedures may be postponed until transport to base hospital facilities. Additional trauma from suture placement may be avoided by temporarily sealing perforations using the hydrogels and related methods described herein, followed by removing the hydrogel by lowering its temperature and allowing it to release.

EXAMPLES

The following examples are put forth to provide those of ordinary skill in the art with a complete disclosure and description of how the compositions, hydrogels, and methods provided herein are made and evaluated, and are intended to be purely exemplary. Thus, the examples are in no way intended to limit the scope of what the inventors regard as their invention. There are numerous variations and combinations of reaction conditions, e.g., component concentrations, desired solvents, solvent mixtures, temperatures, pressures, and other reaction parameters and conditions that may be employed to optimize product characteristics such as stability, purity, mechanical properties, yield, and the like. Such are considered as well within the scope of the present disclosure.

Example 1

PNIPAM Copolymer Synthesis

Copolymer of NIPAM and N-tert-butylacrylamide ($N_{85}T_{15}$): NIPAAM (4.75 g), N-tert-butylacrylamide (0.75 g) and 2,2'azobisisobutyronitrile (AIBN, 0.021 g) were dissolved in a mixture of 37.5 ml of dry tetrahydrofuran and 12.5 ml of benzene. The magnetically stirred solution was degassed, heated to 50° C. for 24 hours under positive nitrogen pressure, and allowed to cool. The reaction mixture was filtered (0.45μ Teflon filter) and the filtrate volume reduced by half. Ether was added with mixing to precipitate the copolymer. The precipitate was filtered off, washed with ether, and dried under vacuum to yield dry 4.64 gram of copolymer product.

Copolymer molar mass moment and polydispersity were characterized:

TABLE 3

| Molar mass moments (g/mol) | Polydispersity |
|---|---|
| $M_n$ 6.624 × $10^5$ (±1.506%) | $M_w/M_n$ 1.078 (±2.467%) |
| $M_p$ 4.775 × $10^5$ (±1.025%) | $M_z/M_n$ 1.187 (±5.541%) |
| $M_w$ 7.143 × $10^5$ (±1.954%) | |
| $M_z$ 7.862 × $10^5$ (±5.333%) | |

In the next step, 10%, 15%, 20% and 30.% solutions were prepared by dissolving the copolymer in DI water by using a horn sonicator to provide representative hydrogels.

Copolymer of NIPAM and Butylacrylate: This copolymer was obtained from Sigma Aldrich (molecular weight: $M_n$ 30,000). Aqueous mixtures: 10%, 15%, 20% and 30% weight percent solids were prepared.

The following table provides a summary of exemplary hydrogels that were evaluated.

Example 2

Adhesion Evaluation

Free-standing pNIPAM-based gels as described in Example 1 were synthesized using a wet chemistry approach, characterized and stored at low temperature prior to use. Adhesion to dissected cadaveric porcine scleral tissue was characterized using a uniaxial tension tester to test under ideal normal force conditions.

An in vitro cadaveric porcine eye model was utilized to assess the ability of the gels to seal penetrating incisions through the sclera, mimicking clinical cases. (Kaja, et al., *Clinical Ophthalmology* (Auckland, NA), 2012; 6:305-309; Lopez-Guajardo, L., et al., *Invest. Ophthalmol Vis Sci.* 2011; Jun. 8; 52(7):4080-4), Adhesion in each test was compared against medical-grade cyanoacrylate glue and sutures, respectively. Real-time IOP (intraocular pressure) was tracked in the whole porcine eye using 19-gauge catheter pressure transducer inserted through the pars plana.

The studies were conducted to assess one or more of the following: whether the pNIPAM-copolymer gels are capable of (i) meeting the adhesion performance of cyanoacrylate in uniaxial tension testing, (ii) preventing hypotony in a cadaveric porcine eye, and/or maintain Iop comparable to suture. Additionally, the copolymers were assessed to determine whether hydrogels as provided herein comprising the pNIPAM-based copolymers can be removed using a temperature lowering protocol.

Using a modified syringe device designed to administer the hydrogels provided herein, the co-polymer was carefully injected into the posterior chamber of the eye near the perforation, and, while continuously deploying the co-polymer, the syringe was slowly retracted from the perforation, leaving behind a trail of co-polymer through the perforation tract. At the exterior surface of the sclera, additional co-polymer was deposited, creating a mushroom like "cap" on the ocular surface. The polymer was allowed to settle for several seconds, enabling it to heat up and dehydrate. After, a scalpel was used to carefully cut away the surface cap. The table below provides a summary of PNIPAM-copolymers/hydrogels evaluated, the ocular pressures maintained, and whether or not they passed the in vitro IOP test. A series of PNIPAM co-polymer preparations were tested in this manner and were given a pass if they were able to maintain ocular pressures above 70 mm Hg (an arbitrary performance criterion). At least five different preparations met the foregoing criterion, and an additional two preparations were able to maintain pressures up to 40 mm Hg, or twice a clinically high IOP level. As can be seen, while all of the PNIPAM compositions failed to maintain an ocular pressure, several of the illustrative copolymer-based hydrogels were able to maintain a measurable ocular pressure.

TABLE 4

| | PNIPAM | PNIPAM:N-tert Butylacrylamide ($A_xT_y$) | PNIPAM:Butylacrylate ($N_xBA_y$) |
|---|---|---|---|
| Chemical Formulae: | $(C_6H_{11}NO)_x$ | $(C_6H_{11}NO)_x:(C_7H_{13}NO)_y$ | $(C_6H_{11}NO)_x:(C_7H_{12}O_2)_y$ |
| Co-Polymer Ratios Tested: | N/A | (85:15) | (95:5); (88:12) |
| Average Molecular Weights: | 2.864 × $10^5$ | 5.55 × $10^5$ to 6.624 × $10^5$ | 3.00 × $10^4$ |
| Percent Aqueous Solution Concentrations Tested: | 10%, 14.2%, 25%, 30%, 43.2% | 10%, 15%, 20%, 30% | 10%, 20%, 30% |
| LCST (° C.): | 32 | 25 | 14-16 |

TABLE 5

| Compound | Co-P Ratio | LCST | MW (Avg) | % [Aqueous] | Maximum Pressure Held (mmHg) | Pass/Fail |
|---|---|---|---|---|---|---|
| PNIPAM | N/A | 32 | $2.864 \times 10^5$ (±2.474%) | 0.8 | 0 | F |
| PNIPAM | N/A | 32 | $2.864 \times 10^5$ (±2.474%) | 2 | 0 | F |
| PNIPAM | N/A | 32 | $2.864 \times 10^5$ (±2.474%) | 5.26 | 0 | F |
| PNIPAM | N/A | 32 | 10,000 | 10.0 | 0 | F |
| PNIPAM | N/A | 32 | 10,000 | 14.2 | 0 | F |
| PNIPAM | N/A | 32 | 10,000 | 25.0 | 0 | F |
| PNIPAM | N/A | 32 | 10,000 | 30.0 | 0 | F |
| PNIPAM | N/A | 32 | 10,000 | 43.2 | 0 | F |
| PNIPAM:n-tert | 85:15 | 25 | $1.038 \times 10^5$ (±2.583%) | No | No | No |
| PNIPAM:n-tert | 85:15 | 25 | $6.624 \times 10^5$ (±1.506%) | 10.0 | 0 | F |
| PNIPAM:n-tert | 85:15 | 25 | $6.624 \times 10^5$ (±1.506%) | 15.0 | 0 | F |
| PNIPAM:n-tert | 85:15 | 25 | $6.624 \times 10^5$ (±1.506%) | 20.0 | 40 | F |
| PNIPAM:n-tert | 85:15 | 25 | $6.624 \times 10^5$ (±1.506%) | 30.0 | 77 | P |
| PNIPAM:n-tert | 85:15 | 25 | $5.55 \times 10^5$ (±1.472%) | 10.0 | 0-10 | F |
| PNIPAM:butylacrylate | 95:5 | 25 | $3 \times 10^4$ | 10.0 | 0 | F |
| PNIPAM:butylacrylate | 95:5 | 25 | $3 \times 10^4$ | 15.0 | 77.4 | P |
| PNIPAM:butylacrylate | 95:5 | 25 | $3 \times 10^4$ | 20.0 | 77.2 | P |
| PNIPAM:butylacrylate | 95:5 | 25 | $3 \times 10^4$ | 30.0 | 77.9 | P |
| PNIPAM:butylacrylate | 88:12 | 14-16 | $3 \times 10^4$ | 10.0 | 0 | F |
| PNIPAM:butylacrylate | 88:12 | 14-16 | $3 \times 10^4$ | 15.0 | 40 | F |
| PNIPAM:butylacrylate | 88:12 | 14-16 | $3 \times 10^4$ | 20.0 | 77.2 | P |
| PNIPAM:butylacrylate | 88:12 | 14-16 | $3 \times 10^4$ | 30.0 | N/A (too viscous) | F |

Results: Synthesized pNIPAM-based copolymer comprising gels predictably and reversibly transitioned between adhesive and non-adhesive states in the desired temperature range for scleral closure. Uniaxial tension testing yielded adhesion performance data comparable to cyanoacrylate with some gel formulations. Intraocular pressure results from the porcine eye model showed that IOP as high as 70-77 mm Hg could be maintained for sustained periods without any leakage. Performance in both tests varied as a function of placement procedure, chemical formula, molecular weight, and gel solution concentration. Gel detachment was successfully achieved by irrigation of the placement site with cold water.

Thus, the instant pNIPAM-based gel adhesives can be effective to provide a rapid and reversible approach for temporarily and satisfactorily sealing scleral penetrations. Such adhesives can provide a new reversible technique for temporary intervention in ocular trauma and other applications.

Example 3

Evaluation of IOP in Rabbits

Baseline was established by measuring IOP on both eyes of two rabbits twice a day (AM and PM) for ten days. IOP was measured using an iCare® Tonovet with a magnetically actuated tonometer. The Tonovet calculates an average reading from six tonometric measurements taken in succession. Four successive readings were taken on each eye, thus 24 measures contributed to the averaged IOP for each eye. For all tonometry measures rabbits were removed from the cage and placed on an evaluation table for 2 minutes to allow the animal to relax. The average IOP results show no significant difference between right and left eyes, and it also shows no significant difference between morning and afternoon average IOP. These results suggested that using an untreated eye as a control to compare against the treated eye in the same animal was a valid assumption.

Implantation Procedure. The first two rabbits underwent surgical procedures to create a 3 mm penetrating injury of the sclera, in the right eye (OD). A 3 mm penetrating incision was created in the sclera, temporal and superior to the cornea, approximately 3 mm from the limbus with the axis of the cut following the perimeter of the limbus. Rabbit 01 (No. 116) was randomized to the adhesive group. Rabbit 02 (No. 117) was randomized to the control (no treatment) group. All surgical procedures performed on these animals were in compliance with IACUC guidance and requirements.

First a 3 mm incision was created and confirmed using calipers. B) Next the hydrogel as described in Example 1 (PNIPAM-butylacrylate copolymer) was deployed using a refrigerated and sterile 1 cc syringe. C) Once deployed, the translucent hydrogel was seen occluding the incision. D) As the hydrogel began to heat up from the inside, the internal portion was seen to transition to opaque. E) As the temperature of the entire hydrogel rose, the rest of the hydrogel transitioned to a white opaque appearance. F) After 5 minutes, the hydrogel was completely opaque white and small droplets of water precipitating from inside the hydrogel were seen on the surface. G) Once set, the "cap" of the hydrogel was clipped using surgical shears, leaving behind H) a small "plug". I) Lastly, the conjunctiva was pulled over the hydrogel plug; no sutures were placed.

A similar 3 mm incision was created in the right eye of rabbit (R02), but no treatment was administered. The eye in R02 was left to heal on its own. IOP was measured on all four eyes in the late afternoon on the same day, and subsequently measured once in the morning and in the afternoon for 5-days.

Figure 5:
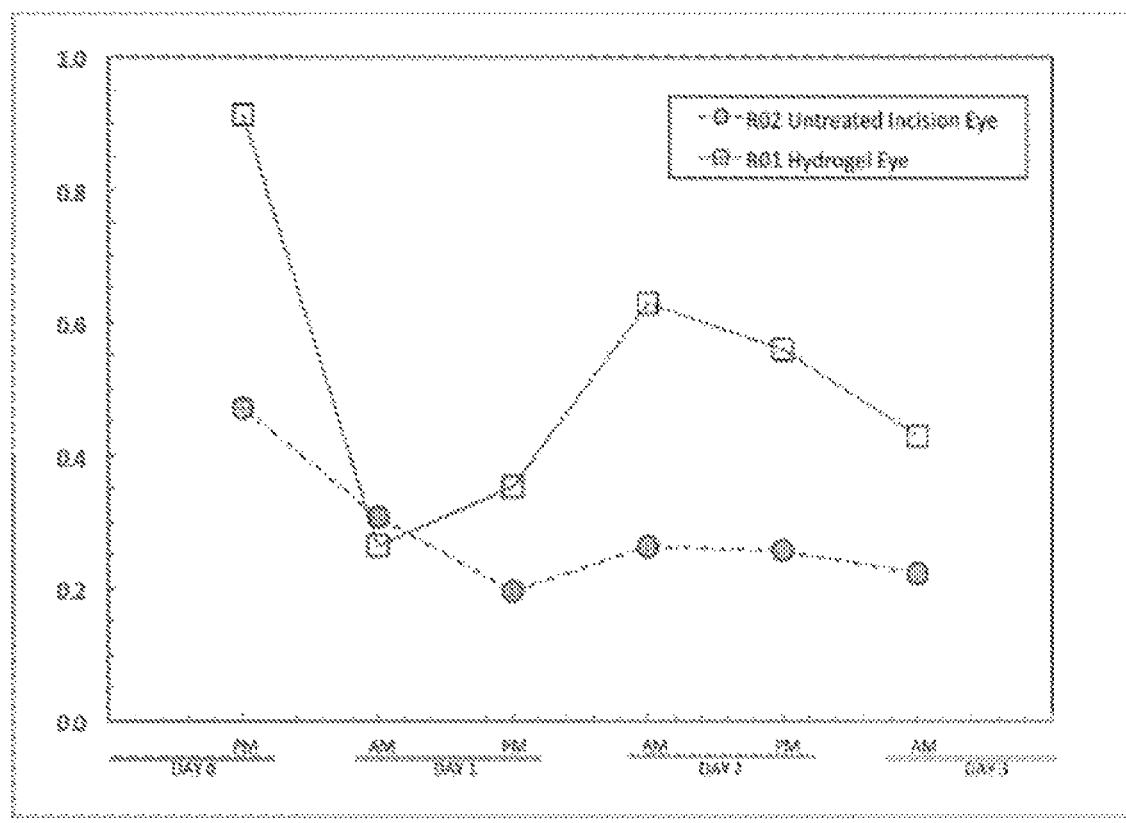
FIG. 5 is a graph demonstrating results from Example 3 in which ocular pressure was plotted for rabbit eyes treated with PNIPAM-copolymer based hydrogels versus untreated eyes over a 72 hour period.

Results: The hydrogel-treated eye maintained higher IOP than the untreated eye for 72 hours. IOP measurements of both eyes for each rabbit (R01 and R02) were measured once in the morning and afternoon for 72-hours following the morning implantation procedure. The IOP measurements of each traumatized eye was normalized against the IOP of the opposite (control) eye in the same rabbit, and plotted in FIG. 5. Over the 72-hour period, the treated eye showed approximately 20%-30% higher IOP vs. the untreated eye, when each was normalized against the contralateral eye (control). The absolute IOP of the traumatized eye without treatment consistently measured 2 mm Hg over the 72-hour period.

At day-5, both rabbits were sedated to evaluate status of incision and to confirm if the hydrogel had migrated or remained in place. Upon inspection, it was determined that the hydrogel was intact. No visible indications of infection or irritation were visible at the immediate site after 5 days.

Example 4

Sterile Hydrogel Deployment in Rabbits Using Exemplary Deployment Device

A method was developed for preparation of a sterile hydrogel comprising a PNIPAM copolymer which can be implanted for in vivo characterization. Pigmented New Zealand rabbits (~2 kg) were randomized to either treatment group (receiving hydrogel) or control (no treatment). Baseline IOP was measured for both eyes (OD and OS) of all animals over a three day period prior to implantation using a Tonovet® rebound tonometer (using canine setting).

Surgical Procedure. Under anesthesia (intramuscular ketamine/xylazine) and topical analgesia (topicaine drops), a small incision was created at the conjunctival junction with the limbus in the temporal quadrant of the right eye (OD). A pocket was created, exposing the scleral surface. A 3 mm linear incision (regular margins) through the scleral wall was then created approximately 2-3 mm away from the edge of the limbus and oriented in a direction tangent to the perimeter of the limbus. Topical antibiotic ointment was applied to the OD of the control group subjects and then allowed to recover. Treatment group OD eyes were then treated with hydrogel.

Hydrogel deployment was performed using a modified, sterile 1 cc syringe. Approximately 0.3 cc to 0.4 cc of sterile hydrogel was extracted from a crimp top vial using the syringe (no needle) with care not to aspirate bubbles into the chamber. Excess hydrogel was wiped away from the tip of the syringe using sterile gauze. The syringe was then placed inside an autoclave-sterilized customized 20 mL syringe. The volume created between the 20 mL syringe and the 1 cc syringe was subsequently filled with a mixture of ammonium nitrate and water to induce an endothermic chemical reaction to cool the hydrogel during deployment. The endothermic reactants were given two minutes to react and bring the hydrogel to the desired temperature. Once ready, a modified, sterile intravenous, polymeric catheter tip was placed onto the end of the 1 cc syringe and the hydrogel was deployed on the eye.

The catheter tip of the injector tool was inserted into the 3 mm incision such that the tip was inside the posterior chamber. Pressure was applied to the plunger of the syringe while the catheter tip was slowly withdrawn, creating a spherical node of hydrogel immediately adjacent and interior to the incision, with a trail of hydrogel filling through the incision tract. Once the catheter tip was completely withdrawn, additional hydrogel was deployed onto the exterior surface of the sclera, forming a "rivet-like" structure with hydrogel caps on both interior and exterior surfaces of the sclera. A total of no more than 0.3 cc of hydrogel was used for all eyes. An incandescent lamp was positioned near the eye so that the hydrogel surface temperature was held at 32.5 C for five minutes. After five minutes, excess hydrogel was trimmed away from the sclera to create a low profile surface. The conjunctiva was then drawn back over the incision area with no sutures placed.

Post-Procedure Monitoring. Animals were checked regularly for signs of infection, discomfort or other adverse effects. Pain medication (ketofen 3 mg/kg) was administered for 48 hrs PRN. IOP was monitored in both eyes of each animal at least twice daily following the surgical procedure. $IOP_{OD}$ for each measurement point was normalized vs the contralateral eye of the same animal ($IOP_{OS}$), to normalize for any effects that may have been caused by stress or medications.

Once water was introduced into the endothermic reaction chamber of the injector tool, time recording of the procedure was initiated. Two minutes were elapsed to allow the reactants to mix. Average surface temperature readings of the injector tool were 9° C., well below the LCST for this hydrogel formulation (LCST=14-16C).

After two minutes, hydrogel deployment was initiated. In all instances when the injector tool's surface temperature was T=9° C., the hydrogel deployed smoothly and easily. After only 30 seconds deployment the hydrogel began to transition to a white opaque color, indicative of its rise above the its lower critical solution temperature (T) and subsequent dehydration. After five minutes, the gel was completely opaque and beads of water were seen on the surface. After five minutes, using surgical scissors, the excess hydrogel "cap" was trimmed away from the surface to create a low profile "flathead" and the conjunctiva was gently drawn over the hydrogel. The average time to deploy the hydrogel in the first series of cases was less than nine minutes (n=7). Based upon these results, it was determined that the instant PNIPAM copolymer-based hydrogels, once deployed to an ocular trauma site, can seal 3 mm penetrating injuries within ten minutes from procedure initiation.

Penetration of the scleral surface with the micro vitreoretinal blade caused an immediate drop in IOP, resulting from the scleral wall being compromised. Eyes sealed by the hydrogel exhibited a refractory period of between 12 to 24 hrs following the procedure, during which the ciliary epithelium of the eye produced aqueous humor to reestablish normal IOP. This was consistent with known rates of aqueous humor production from the eye. In sum, all treatment eyes (i.e. those that received the hydrogel) underwent an approximate 12 hr-24 hr refractory period of low IOP ($IOP_{OD}$=2 mm Hg).

During the procedures, it was observed that preferred deployment of the unsupported hydrogel (i.e., not deposited on a substrate) comprises creation of a "rivet like" structure where a spherical cap of hydrogel is created on the interior surface of the scleral, with hydrogel filling through the perforation, followed by a cap.

Scleral tissue surround the implant sites show no signs of redness, inflammation or bleeding after 48 hrs, suggesting that the hydrogel induces no adverse tissue response.

The components, steps, features, objects, benefits and advantages which have been discussed are merely illustrative. None of them, nor the discussions relating to them, are intended to limit the scope of protection in any way. Numerous other embodiments are also contemplated. These include embodiments which have fewer, additional, and/or different components, steps, features, objects, benefits and advantages. These also include embodiments in which the components and/or steps are arranged and/or ordered differently.

Unless otherwise stated, all measurements, values, ratings, positions, magnitudes, sizes, and other specifications which are set forth in this specification are approximate, not exact. They are intended to have a reasonable range which is consistent with the functions to which they relate and with what is customary in the art to which they pertain.

All articles, patents, patent applications, and other publications which have been cited are hereby incorporated herein by reference.

The invention claimed is:

1. A method for reversibly sealing an ocular perforation, the method comprising applying a temperature-responsive hydrogel to a tear in ocular tissue of a subject in an amount effective to seal the tear, the temperature-responsive hydrogel including a poly(N-isopropylacrylamide) copolymer at a concentration of about 10 weight percent to about 60 weight percent in water, wherein the poly(N-isopropylacrylamide) copolymer (i) is a copolymer of poly(N-isopropylacrylamide) and a second polymer that is either a polymer of N-tert-butylacrylamide or butylacrylate, (ii) has a weight percent ratio of poly(N-isopropylacrylamide) to the second polymer of about 95:5 to about 70:30, and (iii) has a number average molecular weight of about 5,000 to about 5,000,000 Daltons, wherein when exposed to a temperature above its critical solution temperature, the temperature-responsive hydrogel becomes adhesive, and when exposed to a temperature below its critical solution temperature, the temperature-responsive hydrogel becomes less adhesive, wherein the temperature-responsive hydrogel is maintained at a temperature below its critical solution temperature prior to said applying.

2. The method of claim 1, wherein the temperature of the ocular tissue is above the critical solution temperature of the temperature-responsive hydrogel.

3. The method of claim 2, wherein the temperature-responsive hydrogel adheres to the tissue of edges of the tear.

4. The method of claim 1, wherein said applying comprises applying to an inner surface of the eye wall a slight excess of an amount of hydrogel effective to fill a void created by the tear in ocular tissue.

5. The method of claim 4, wherein an ocular pressure is effective to press excess hydrogel against the inner surface of the eye to thereby create an internal ocular seal.

6. The method of claim 1 wherein an adhesive patch comprising the temperature-responsive hydrogel deposited on a polymeric substrate is applied to the tear.

7. The method of claim 6, wherein the polymeric substrate is selected from the group consisting of parylene, poly-lactic acid, polyimide, and polydimethylsiloxane.

* * * * *